United States Patent
Yuan et al.

(10) Patent No.: US 10,538,541 B2
(45) Date of Patent: *Jan. 21, 2020

(54) PHOSPHORAMIDATE COMPOUND AND PREPARATION METHOD AND CRYSTAL THEREOF

(71) Applicant: BrightGene Bio-Medical Technology Co., Ltd., Suzhou, Jiangsu (CN)

(72) Inventors: Jiandong Yuan, Suzhou (CN); Yangqing Huang, Suzhou (CN); Linfeng Miao, Suzhou (CN); Jianing Gu, Suzhou (CN); Chaohua Liang, Suzhou (CN); Zhengye Wang, Suzhou (CN); Zhanli Sun, Suzhou (CN)

(73) Assignee: BrightGene Bio-Medical Technology Co., Ltd., Suzhou, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/754,318

(22) PCT Filed: Sep. 13, 2016

(86) PCT No.: PCT/CN2016/098845
§ 371 (c)(1),
(2) Date: Feb. 22, 2018

(87) PCT Pub. No.: WO2017/045581
PCT Pub. Date: Mar. 23, 2017

(65) Prior Publication Data
US 2018/0244701 A1 Aug. 30, 2018

(30) Foreign Application Priority Data
Sep. 16, 2015 (CN) .......................... 2015 1 0588383

(51) Int. Cl.
C07F 9/22 (2006.01)
C07H 19/10 (2006.01)
C07F 9/02 (2006.01)

(52) U.S. Cl.
CPC .............. *C07F 9/222* (2013.01); *C07F 9/025* (2013.01); *C07H 19/10* (2013.01); *C07B 2200/07* (2013.01); *C07B 2200/13* (2013.01)

(58) Field of Classification Search
None
See application file for complete search history.

(56) References Cited

U.S. PATENT DOCUMENTS

| | | |
|---|---|---|
| 8,618,076 B2 | 12/2013 | Ross et al. |
| 8,642,756 B2 | 2/2014 | Ross et al. |
| 8,841,275 B2 | 9/2014 | Du et al. |
| 9,284,342 B2 | 3/2016 | Ross et al. |
| 9,370,569 B2 | 6/2016 | Smith et al. |
| 9,834,577 B2 | 12/2017 | Dammalapati et al. |
| 10,030,044 B2 | 7/2018 | Dousson et al. |
| 10,092,649 B2 | 10/2018 | Smith et al. |
| 2011/0245484 A1 | 10/2011 | Ross et al. |
| 2011/0251152 A1* | 10/2011 | Ross ...................... C07H 19/06 514/51 |
| 2013/0288997 A1 | 10/2013 | Ross et al. |

FOREIGN PATENT DOCUMENTS

| | | | |
|---|---|---|---|
| CN | 104640444 | 5/2015 | |
| WO | 2005/012327 | 2/2005 | |
| WO | 2012/075140 | 6/2012 | |
| WO | WO-2012075140 A1 * | 6/2012 | ............ C07H 19/06 |
| WO | WO 2013/187978 | 12/2013 | |
| WO | WO 2014/033617 | 3/2014 | |
| WO | WO 2014/058801 | 4/2014 | |
| WO | WO 2014/076490 | 5/2014 | |
| WO | 2015/198058 | 12/2015 | |
| WO | 2016/055769 | 4/2016 | |

OTHER PUBLICATIONS

Slusarczyk, J. Med. Chem. 2014, 57, 1531-1542. (Year: 2014).*
ISA/CN, International Search Report for PCT/CN2016/098845 (dated Dec. 9, 2016).
International Search Report which dated Nov. 15, 2016 in corresponding application No. PCT/CN2016/098847.
ISA/CN, International Search Report for PCT/CN2016/098846 (dated Nov. 30, 2016).

* cited by examiner

*Primary Examiner* — Layla D Berry
(74) *Attorney, Agent, or Firm* — Fish & Richardson P.C.

(57) ABSTRACT

The present disclosure involves a composition enriched in compound 61501b, wherein the compound 61501b has a purity of not less than 90% or more. The composition has a significant advantage in preparing a high-purity compound Sp-1. In addition, the present disclosure also provides a preparation method of the composition enriched in compound 61501b. The method adopts a crystallization technique to perform separation and purification, has a simple and convenient operation and good reproducibility, and therefore the compound 61501b in the prepared composition has high purity and quality. Further, the present disclosure also involves a novel crystal form of compound 61501b.

14 Claims, 5 Drawing Sheets

PHOSPHORAMIDATE COMPOUND AND PREPARATION METHOD AND CRYSTAL THEREOF

TECHNICAL FIELD

The present disclosure relates to the field of medicinal chemistry, and in particular to a phosphoramidate compound, its preparation method and a crystal form thereof. The present disclosure also relates to a composition comprising a high-purity single isomer of the phosphoramidate compound, a preparation method thereof and a crystal form thereof.

BACKGROUND

NUC-1031 is a prodrug of gemcitabine developed by NuCana BioMed Ltd., and is currently in Phase II clinical trials for the treatment of cancers such as advanced solid tumors, pancreatic cancer and breast cancer. The CAS of NUC-1031 is 840506-29-8 and NUC-1031 has a structure as represented by formula 1 below, and the following formulae $R_P$-1 and $S_P$-1 are respectively the enantiomers of phosphorus atom P of NUC-1031:

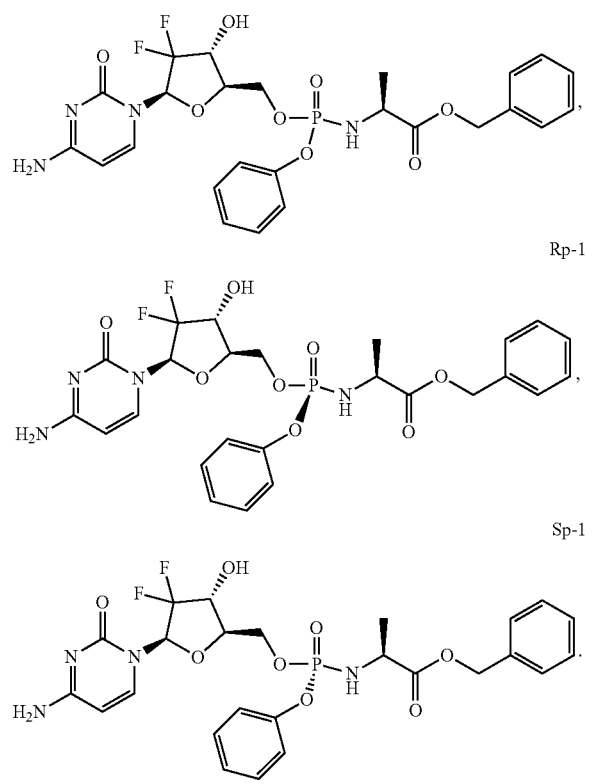

WO2005012327 discloses a great number of phosphoramidate nucleoside prodrugs, and these phosphoramidate nucleoside prodrugs are mostly present in the form of a mixture of the enantiomers(R/S) of P. It is rather difficult to isolate a high-purity single isomer according to the conventional separation methods such as the separation by chiral column or the separation by column chromatography. As reported in the literature "Application of ProTide Technology to Gemcitabine: A Successful Approach to Overcome the Key Cancer Resistance Mechanisms Leads to a New Agent (NUC-1031) in Clinical Development" (*Journal of Medicinal Chemistry*, Volume 57, Issue 4, Pages 1531-1542), NUC-1031 was prepared by purification via a silica gel column, and the contents of the isomers finally obtained were 48% and 52%, respectively.

At present, the preparation methods of the single enantiomer of the phosphoramidate nucleoside prodrug P are rarely reported in the prior art. Since the two enantiomers of chiral P in this kind of molecular structure are very similar in structure and polarity, it becomes very difficult to isolate a high-purity single isomer from the racemic mixture of NUC-1031, and in particular, it is even more difficult to balance purity and yield simultaneously in the purification process.

Isolating single isomers from enantiomers, studying their biological activities respectively, and studying the pharmacological effects, toxic side effects, adverse reactions, or the like of the phosphoramidate nucleoside prodrugs to develop similar drugs with better activity and less toxic side effects will be of great significance.

The compound 61501b, when used as a key intermediate for the preparation of the single isomers of a variety of phosphoramidate nucleoside prodrugs, can significantly improve the purity of the single isomers, increase the production efficiency, reduce the production costs, and provide qualified raw materials for the clinical study of the single isomers of the phosphoramidate nucleoside prodrugs.

The CAS of the compound 61501b is 1392015-79-0, and its structure is shown as below,

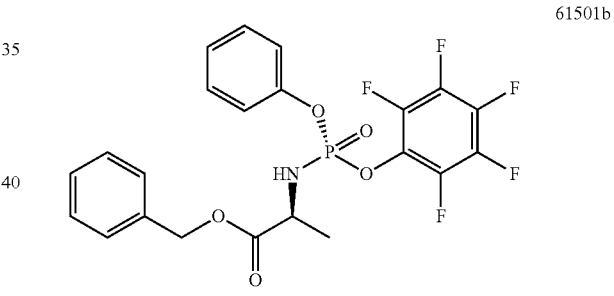

In the prior art, there are few studies about the preparation methods, the crystal forms, and the like of the compound 61501b. Only the structure of the compound 61501b is disclosed in WO2012075140, but the related information about the preparation methods, the crystal forms, and the like of the compound 61501b has not been reported in any literature at present. Therefore, there is an urgent need to develop a composition containing the high-purity compound 61501b that meets the market demand and a method for preparing the high-purity compound 61501b suitable for industrial production.

SUMMARY

In order to solve the above problems, in one aspect, the present disclosure provides a composition enriched in compound 61501b;

In another aspect, the present disclosure provides a method for preparing the composition enriched in compound 61501b;

In another aspect, the present disclosure also provides a crystal of the compound 61501b;

In yet another aspect, the present disclosure further provides the use of the compound 61501b in the preparation of the compound S$_P$-1,

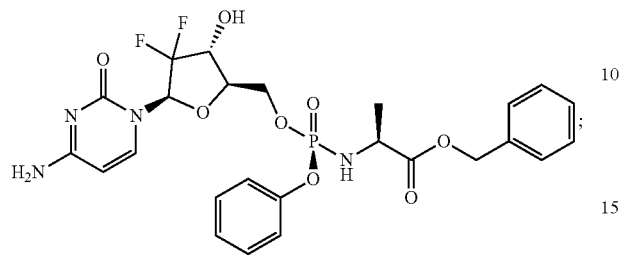

S$_P$-1

First of all, the present disclosure provides a composition enriched in compound 61501b, the purity of the compound 61501b in the composition is not less than 90%,

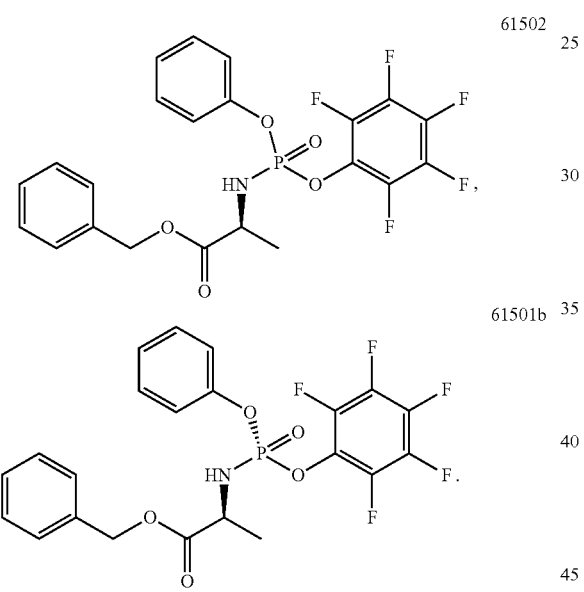

61502

61501b

Further, the purity of the compound 61501b in the composition is not less than 95%; and still further, the purity of the compound 61501b in the composition is not less than 99%.

In another aspect, the present disclosure provides a method for preparing the composition enriched in compound 61501b, comprising the following steps:

(1) reacting a compound (61501h) with a compound (61501g) under alkaline conditions, and then reacting with a compound (61501f) to obtain a compound 61502:784

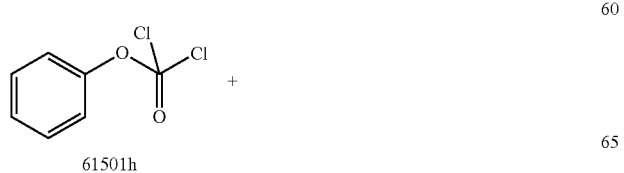

61501h

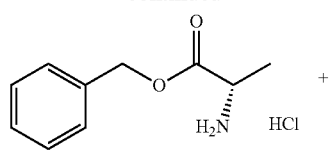

61501g

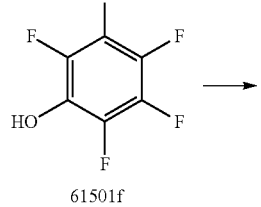

61501f

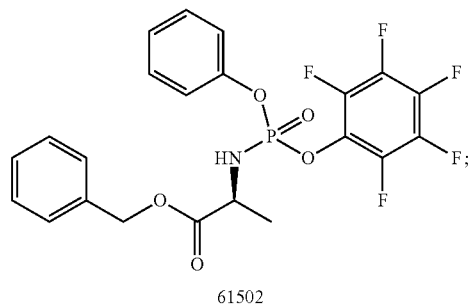

61502 and (2) obtaining the composition enriched in compound 61501b by the isomer separation of the compound 61502:

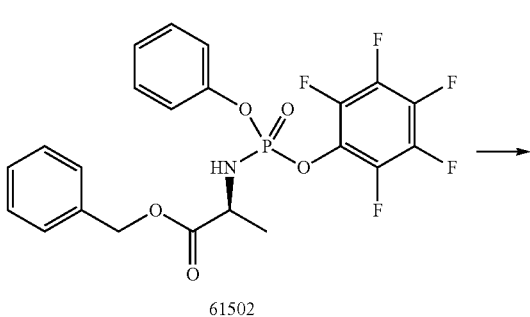

61502

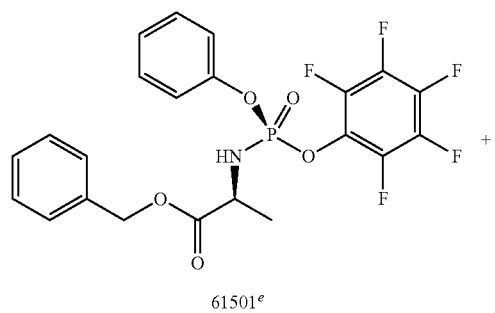

61501$^e$

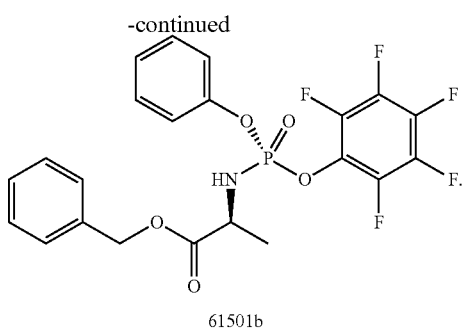

61501b

In the above method, in the step (1), the reaction is preferably carried out under the protection of $N_2$, the compound (61501h) is added to a suitable solvent (such as dichloromethane, isopropanol, DMF and dioxane), and then the compound (61501g) and a suitable base (such as triethylamine, DIPEA, NMM, pyridine and piperidine) are added at a suitable temperature (preferably −80° C.); after the dropwise addition is complete, it is preferred that the reaction is carried out at room temperature overnight and then, to the reaction solution, the compound (61501f) and a suitable base (such as triethylamine, DIPEA, NMM, pyridine and piperidine) are added; after the reaction is complete, the solvent is removed by distillation, ethyl acetate and water are added for extraction, and the target compound (61502) is obtained by separation.

In the above method, the method for isomer separation in the step (2) comprises: a first step of dissolving the compound 61502 in an organic solvent and stirring for dissolving; and a second step of adding an anti-solvent dropwise to the above solution system, and crystallizing, thereby giving the compound 61501b.

Wherein the organic solvent comprises at least one of the following: $C_{1-8}$ alcohols, $C_{2-8}$ ethers, $C_{3-7}$ ketones, $C_{3-7}$ esters, $C_{1-2}$ chlorocarbons, and $C_{2-7}$ nitriles. It is still further preferred that the organic solvent is selected from ethyl acetate, tert-butyl methyl ether, isopropanol or tetrahydrofuran.

Wherein the anti-solvent comprises at least one of the following: $C_{5-12}$ saturated hydrocarbons, $C_{6-12}$ aromatic hydrocarbons, and petroleum ether; and more preferably, the anti-solvent is selected from petroleum ether or hexane.

Further, in the above method, the volume ratio of the organic solvent to the anti-solvent is 1:2 to 10 (v/v), and preferably 1:4 to 6 (v/v); the amount ratio of the compound 61502 to the organic solvent is 1:1 to 10 (w/v), and preferably 1:1.25 to 2.5 (w/v).

In another preferred embodiment, the organic solvent is selected from ethyl acetate, and the anti-solvent is selected from petroleum ether.

More preferably, in the above method, the method for isomer separation in the step (2) comprises: a first step of dissolving the compound 61502 in ethyl acetate, and stirring at room temperature for dissolving; and a second step of adding petroleum ether dropwise to the above solution system, crystallizing and filtering, thereby giving the compound 61501b. It is preferred that the amount ratio of the compound 61502 to ethyl acetate is 1:1.25 to 2.5 (w/v), and the amount ratio of ethyl acetate to petroleum ether is 1:4 to 6 (v/v).

In another preferred embodiment, the temperature of the stirring for dissolving and crystallizing in the step (2) is 10° C. to 50° C.; and more preferably, the temperature is 25° C. to 30° C.

Preferably, in the composition enriched in compound 61501b prepared by the above method, the purity of the compound 61501b is not less than 90%, and it is further preferred that the purity of the compound 61501b in the composition is not less than 95% or 99%.

In another aspect of the present disclosure, a crystal of the compound 61501b is provided, and an X-ray powder diffraction pattern of the crystal has peaks at the following 2θ angles: 7.2°±0.3°, 9.6°±0.3° and 23.1°±0.3°.

In another preferred embodiment of the present disclosure, an X-ray powder diffraction pattern of the crystal has peaks at the following 2θ angles: 7.2°±0.3°, 8.1°±0.3°, 9.6°±0.3°, 10.5°±0.3°, 14.4°±0.3° and 23.1°±0.3°.

In another preferred embodiment of the present disclosure, an X-ray powder diffraction pattern of the crystal has peaks at the following 2θ angles: 5.3°±0.3°, 7.2°±0.3°, 8.1°±0.3°, 9.6°±0.3°, 10.5°±0.3°, 11.6°±0.3°, 14.4°±0.3°, 19.4°±0.3°, 21.1°±0.3° and 23.1°±0.3°.

In another preferred embodiment of the present disclosure, the crystal has an X-ray powder diffraction pattern substantially as shown in FIG. 1.

Methods for determining the X-ray powder diffraction of crystals are known in the art. For example, using a Bruker D8 Advanced model X-ray powder diffractometer, a pattern is obtained using a copper radiation target at a scanning speed of 2° per minute.

In another aspect, the crystal of the above compound 61501b has a purity of 80% by weight or more with respect to the total amount of the compound 61502b. Preferably, it has a purity of 90% by weight or more with respect to the total amount of the compound 61502b.

In another aspect, the present disclosure also provides the use of the compound 61501b in the preparation of the compound $S_P$-1,

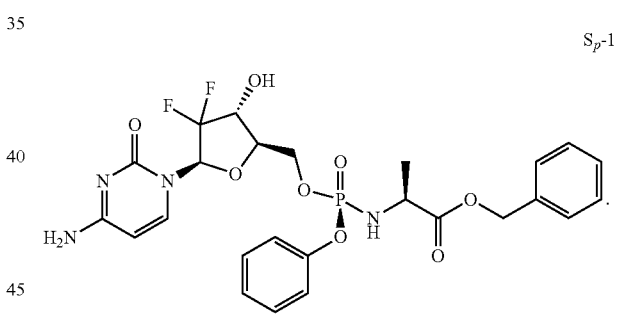

$S_P$-1

Specifically, a compound (61501a) is prepared by reacting the compound (61501b) with a compound (61501c), and the hydroxyl protective group of the compound (61501a) is deprotected to obtain the compound ($S_P$-1):

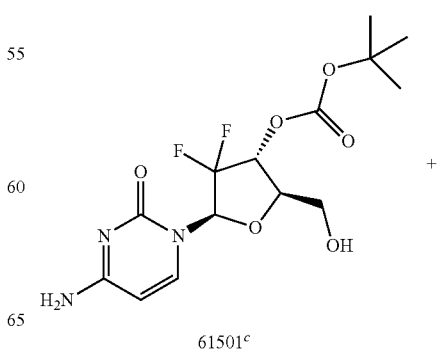

+

61501c

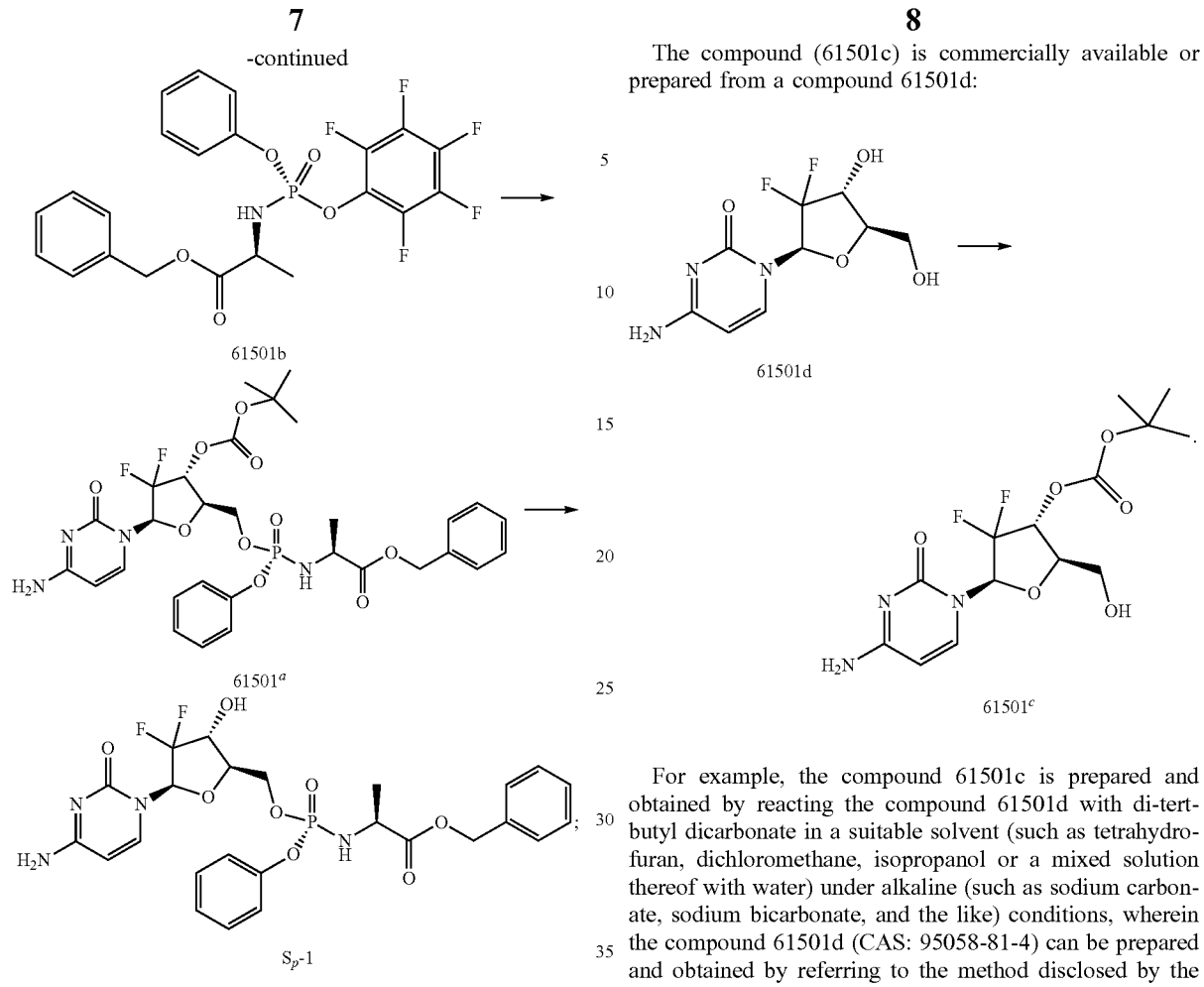

In the above method, it is preferred that under the protection of nitrogen gas, a Grignard reagent (such as tert-butylmagnesium chloride, and preferably a solution of tert-butylmagnesium chloride in tetrahydrofuran) is added to the compound 61501c in a suitable solvent (such as tetrahydrofuran and dichloromethane) under the conditions of a suitable temperature (such as −10° C. to 5° C., and preferably 0° C.) to react for about 0.5 to 3 hours; thereafter, the compound 61501b obtained by separation in the step (2) is added for reaction, and till the reaction is complete, water is added to the reaction solution; then ethyl acetate is used for extraction to give the crude compound 61501a; the above crude product can be further purified by a conventional method such as crystallization, column chromatography, and the like, and it is preferred to obtain the compound 61501a by purification using silica gel column chromatography with dichloromethane-methanol as an eluent. Preferably, under the protection of nitrogen gas, the hydroxyl protective group of the compound 61501a is deprotected by catalysis using an acid (such as trifluoroacetic acid, and hydrogen chloride/ethyl acetate) in a suitable solvent (such as dichloromethane and ethyl acetate) under the conditions of a suitable temperature (such as −10° C. to 5° C., and preferably 0° C.); after the reaction is complete, a aqueous solution of weak base (such as a saturated solution of sodium bicarbonate) and an organic solvent (such as ethyl acetate) are added, the organic layer is separated, concentrated and dried to give the crude compound $S_P$-1; it is further preferred to purify the above crude product, for example, by using silica gel column chromatography with dichloromethane-methanol as an eluent.

The compound (61501c) is commercially available or prepared from a compound 61501d:

For example, the compound 61501c is prepared and obtained by reacting the compound 61501d with di-tert-butyl dicarbonate in a suitable solvent (such as tetrahydrofuran, dichloromethane, isopropanol or a mixed solution thereof with water) under alkaline (such as sodium carbonate, sodium bicarbonate, and the like) conditions, wherein the compound 61501d (CAS: 95058-81-4) can be prepared and obtained by referring to the method disclosed by the literature "An efficient large-scale synthesis of gemcitabine employing a crystalline 2,2-difluoro-α-ribofuranosyl bromide" (Tetrahedron [0040-4020] Chang, Young-Kil, 2010, Volume 66, Issue 30, pages: 5687-5691), or obtained by purchase.

The term "purified" as described herein refers to the purity of a given compound. For example, when a given compound is the major component of a composition, said compound is "purified", i.e., at least 50% w/w purity (i.e., the weight ratio of said compound to said composition). Thus, "purified" includes at least 50% w/w purity, at least 60% w/w purity, at least 70% w/w purity, at least 80% purity, at least 85% purity, at least 90% purity, at least 92% purity, at least 94% purity, at least 96% purity, at least 97% purity, at least 98% purity, at least 99% purity, at least 99.5% purity and at least 99.9% purity, wherein "substantially pure" includes at least 97% purity, at least 98% purity, at least 99% purity, at least 99.5% purity and at least 99.9% purity.

The term "about" (also denoted by "~") means that the referred value is a part of the range ranging within the standard error of the test.

The expression "substantially as shown in . . . " a specified XRPD pattern means that the peak positions shown in the XRPD pattern are substantially the same, within visual inspection or resort to selected peak listings (±0.3° 2θ). One of ordinary skill understands that the intensities can vary depending on the sample.

The terms "purity" and "purified" as described in the present disclosure refer to the purity of a given compound. For example, when a given compound is the major component of a composition, said compound is purified, and the purity of said compound is at least 80% w/w (i.e., the weight ratio of said compound to said composition), at least 90% w/w, at least 95% w/w, at least 99% w/w. The term "rich" means that the defined compound is the major component of a composition. For example, "a composition enriched in compound 61501b" means that the compound 61501b is the major component in said composition.

$C_{1-8}$ alcohols refer to linear/branched and/or cyclic/acyclic alcohols having said number of carbon atoms. $C_{1-8}$ alcohols include (but are not limited to) methanol, ethanol, n-propanol, isopropanol, isobutanol, hexanol, and cyclohexanol. $C_{2-8}$ ethers refer to linear/branched and/or cyclic/acyclic ethers having said number of carbon atoms. $C_{2-8}$ ethers include (but are not limited to) dimethyl ether, diethyl ether, diisopropyl ether, di-n-butyl ether, methyl tert-butyl ether (MTBE), tetrahydrofuran, and dioxane. $C_{3-7}$ ketones refer to linear/branched and/or to cyclic/acyclic ketones having said number of carbon atoms. $C_{3-7}$ ketones include (but are not limited to) acetone, methyl ethyl ketone, butanone, methyl isobutyl ketone, methyl butyl ketone, and cyclohexanone. $C_{3-7}$ esters refer to linear/branched and/or cyclic/acyclic esters having said number of carbon atoms. $C_{3-7}$ esters include (but are not limited to) ethyl acetate, propyl acetate, n-butyl acetate, and the like. $C_{1-2}$ chlorocarbons refer to chlorocarbons having said number of carbon atoms. $C_{1-2}$ chlorocarbons include (but are not limited to) chloroform, methylene chloride (DCM), carbon tetrachloride, 1,2-dichloroethane, and tetrachloroethane. $C_{2-7}$ nitriles refer to nitriles having said number of carbon atoms. $C_{2-7}$ nitriles include (but are not limited to) acetonitrile, propionitrile, and the like. $C_{6-12}$ aromatic hydrocarbons refer to substituted and unsubstituted hydrocarbons having phenyl group(s) as the main chain thereof. Preferred hydrocarbons include benzene, xylene, toluene, chlorobenzene, o-xylene, m-xylene, p-xylene, xylenes, and more preferably toluene.

The composition enriched in compound 61501b provided by the present disclosure, especially when the purity of the compound 61501b therein is not less than 95% or more, has significant advantages in the preparation of the high-purity compound $S_P$-1. Through a large number of experiments, the inventors found that the higher the purity of the compound 61501b in the composition enriched in compound 61501b is, the higher is the purity of the prepared compound $S_P$-1. Secondly, the method for preparing the composition enriched in compound 61501b provided in the present disclosure has a simple and convenient operation as well as good reproducibility, and the compound 61501b in the prepared composition has high purity and good quality. In addition, the present disclosure also provides a novel crystal form of the compound 61501b.

BRIEF DESCRIPTION OF THE DRAWINGS

FIG. 1 shows an X-ray powder diffraction (XRPD) pattern of the compound 61501b prepared according to the method of Example 2; wherein:

| Labe | Position | Intensity | FWHM | FWHM (sec) | LHM Position | LHM Intensity | RHM Position | RHM Intensity |
|---|---|---|---|---|---|---|---|---|
| 1 | 5.2804 | 2979.8 | 0.535 | 1926.8646 | 4.9427 | 1489.9214 | 5.4779 | 1489.9214 |
| 2 | 7.1823 | 18790 | 0.21 | 757.3567 | 7.0672 | 9394.9969 | 7.2775 | 9394.9969 |
| 3 | 8.1302 | 11046 | 0.216 | 778.4982 | 8.0101 | 5522.8734 | 8.2263 | 5522.8734 |
| 4 | 9.6044 | 27189 | 0.192 | 689.8162 | 9.4976 | 13594.562 | 9.6893 | 13594.562 |
| 5 | 10.5144 | 11307 | 0.21 | 757.349 | 10.3969 | 5653.3292 | 10.6072 | 5653.3292 |
| 6 | 11.6526 | 6440 | 0.233 | 837.5713 | 11.5201 | 3219.999 | 11.7527 | 3219.999 |
| 7 | 13.7162 | 2308.4 | 0.376 | 1352.2786 | 13.4872 | 1154.2135 | 13.8628 | 1154.2135 |
| 8 | 14.3802 | 10937 | 0.223 | 803.8413 | 14.2503 | 5468.3332 | 14.4736 | 5468.3332 |
| 9 | 15.7764 | 3340.2 | 0.299 | 1074.523 | 15.6113 | 1670.1175 | 15.9098 | 1670.1175 |
| 10 | 16.1325 | 3149.2 | 0.358 | 1289.0177 | 15.927 | 1574.6181 | 16.2851 | 1574.6181 |
| 11 | 18.438 | 5503.7 | 0.224 | 806.0012 | 18.3048 | 2751.8554 | 18.5285 | 2751.8554 |
| 12 | 19.4135 | 8377 | 0.234 | 842.2961 | 19.2702 | 4188.4999 | 19.5041 | 4188.4999 |
| 13 | 21.0649 | 6813.1 | 0.236 | 848.0567 | 20.9271 | 3406.5369 | 21.1627 | 3406.5369 |
| 14 | 22.28 | 2369.7 | 0.355 | 1276.1935 | 22.0587 | 1184.8381 | 22.4112 | 1184.8381 |
| 15 | 23.1413 | 14030 | 0.222 | 800.8144 | 23.0087 | 7014.8613 | 23.2311 | 7014.8613 |
| 16 | 23.4262 | 2415.7 | 0.301 | 1083.961 | 23.2757 | 1207.8268 | 23.5768 | 1207.8268 |
| 17 | 27.5688 | 2471.8 | 0.466 | 1677.2255 | 27.3358 | 1235.8845 | 27.8017 | 1235.8845 |
| 18 | 32.3292 | 2274.1 | 0.43 | 1547.5242 | 32.1143 | 1137.0724 | 32.5442 | 1137.0724 |

Figure 2:
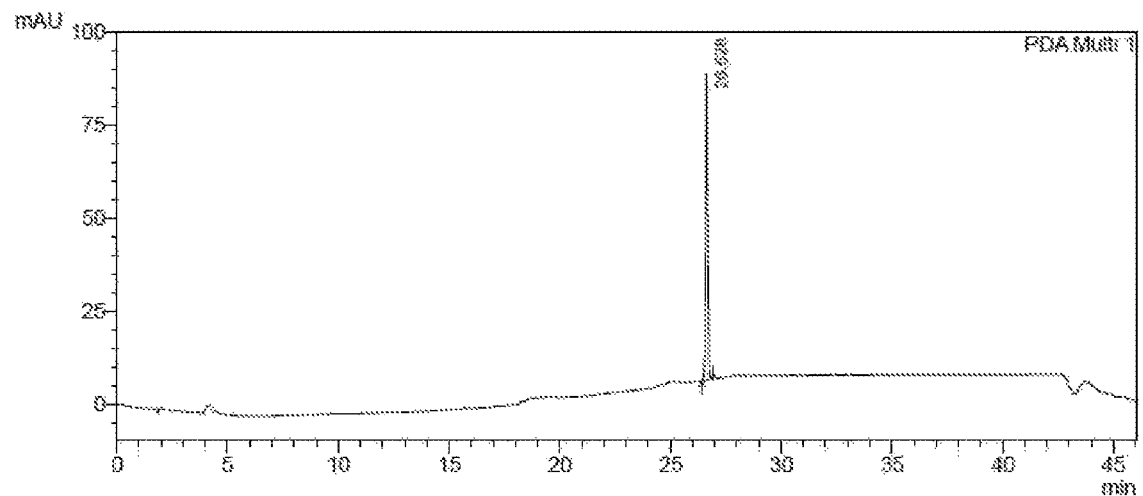

FIG. 2 shows the purity of the compound 61501b by HPLC prepared according to the method of Example 2, wherein the HPLC purity of the compound (61501b) is 100%; and the peak data thereof is shown as below.

| Peak # | Name | Retention time | Area | Peak height | Area % |
|---|---|---|---|---|---|
| 1 | 61501b | 26.628 | 566450 | 82468 | 100 |
| Total | | | 566450 | 82468 | 100 |

Figure 3:
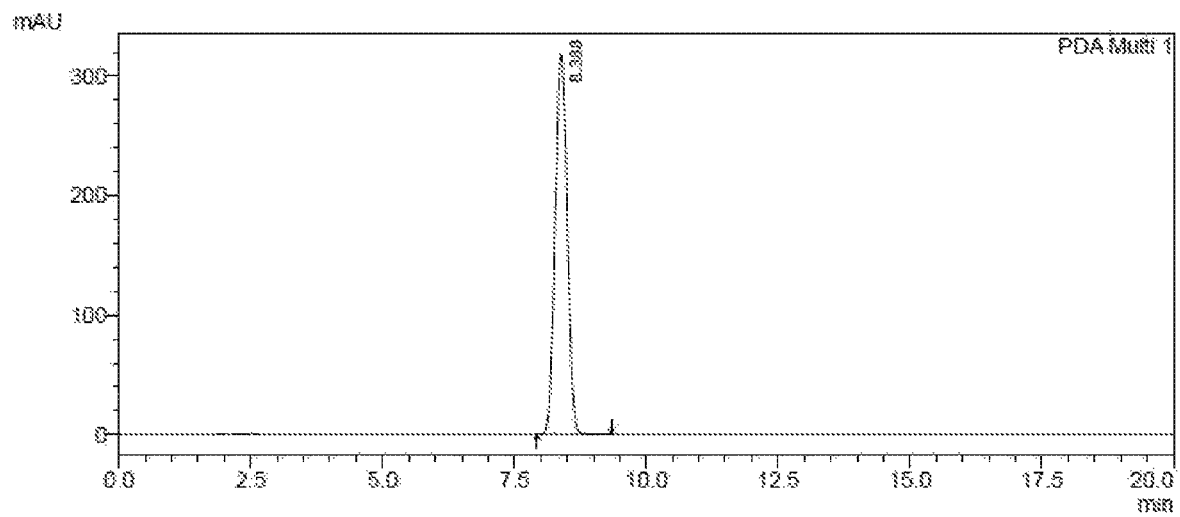

FIG. 3 shows an HPLC analysis chromatogram of the compound $S_P$-1 prepared according to the method of Example 4, Wherein the HPLC purity of the compound $S_P$-1 is 100%, and the peak data thereof is shown as below.

| Peak # | Retention time | Area | Peak height | Area % |
|---|---|---|---|---|
| 1 | 8.388 | 5096820 | 317635 | 100 |
| Total | | 5096820 | 317635 | 100 |

Figure 4:
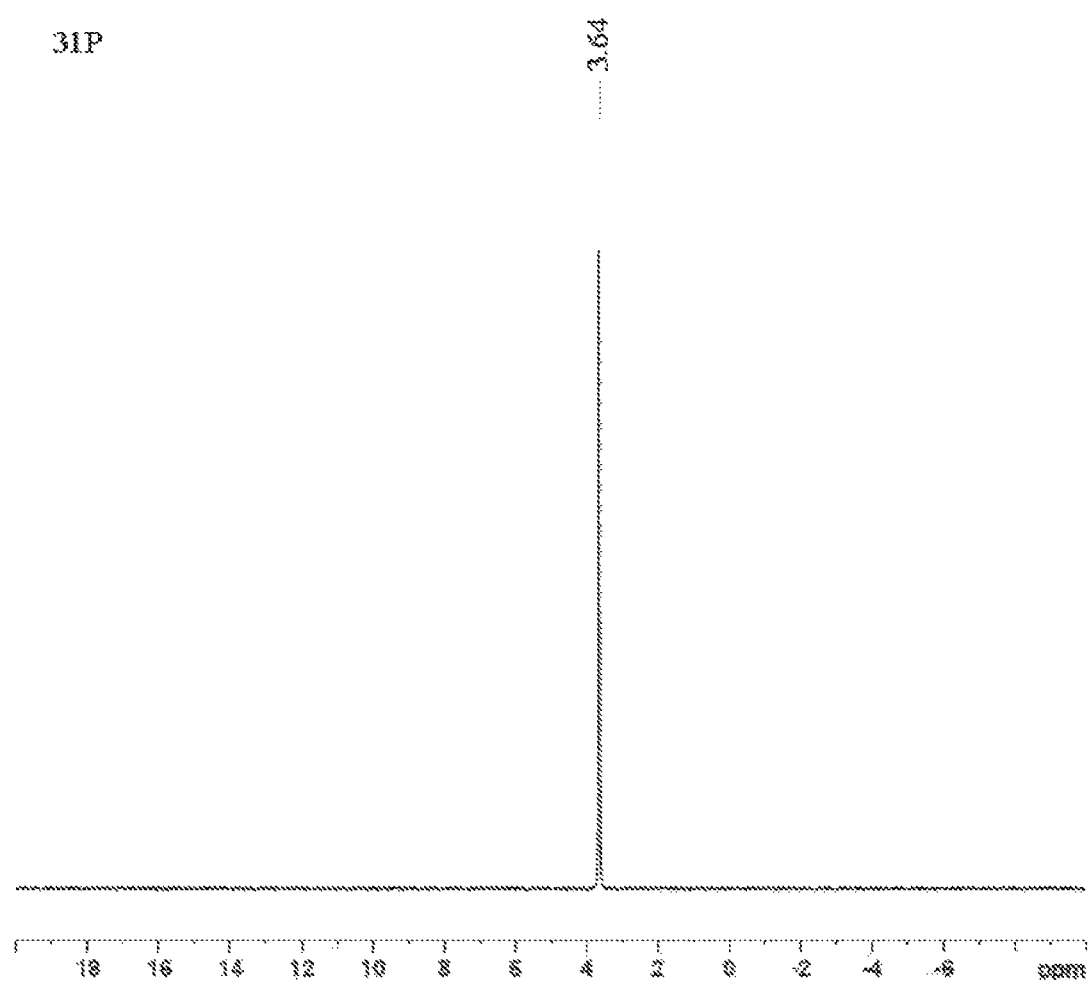

FIG. 4 shows the $^{31}$P-NMR spectrum of the compound $S_P$-1 prepared according to the method of Example 4, in which one peak is at $\delta_P$ 3.64.

Figure 5:
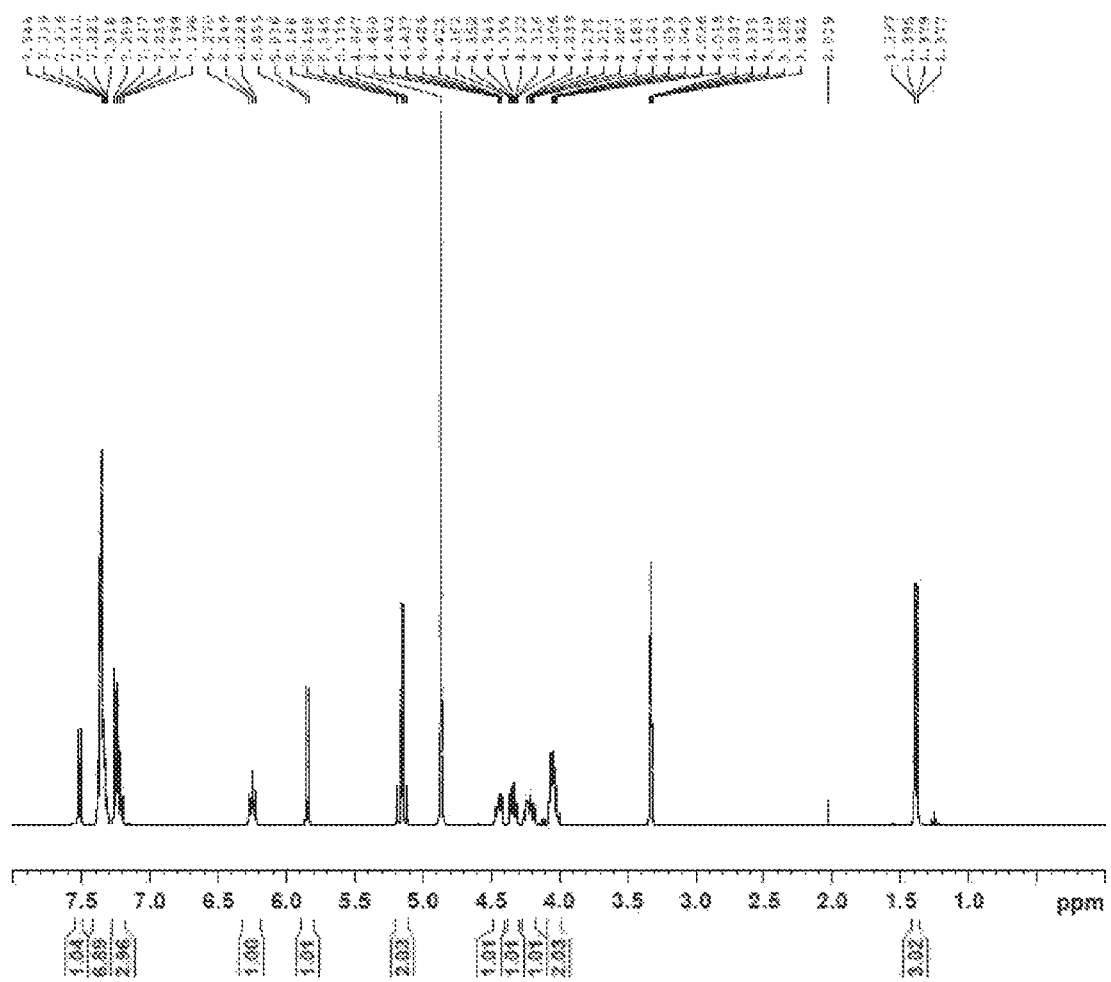

FIG. 5 shows the $^1$H-NMR spectrum of the compound $S_P$-1 prepared according to the method of Example 4.

Figure 6:
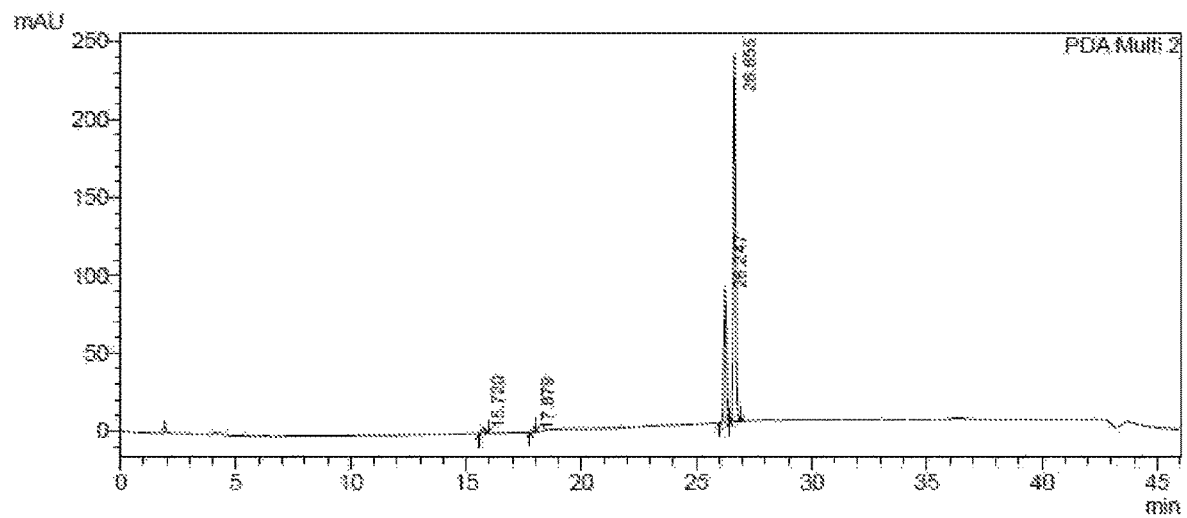

FIG. 6 shows an HPLC chromatogram of the compound (61502) used in the preparation of the compound 1 in Comparative Example 1. The ratio of the isomers thereof, i.e., 61501e to 61501b is 26.25%-72.03, and the peak data thereof is shown as below.

| Peak # | Name | Retention time | Area | Peak height | Area % |
|---|---|---|---|---|---|
| 1 | | 15.720 | 32073 | 3645 | 1.40 |
| 2 | | 17.879 | 7237 | 1012 | 0.32 |
| 3 | 61501e | 26.247 | 599792 | 86409 | 26.25 |
| 4 | 61501b | 26.655 | 1645757 | 235596 | 72.03 |
| Total | | | 2284859 | 326662 | 100 |

Figure 7:
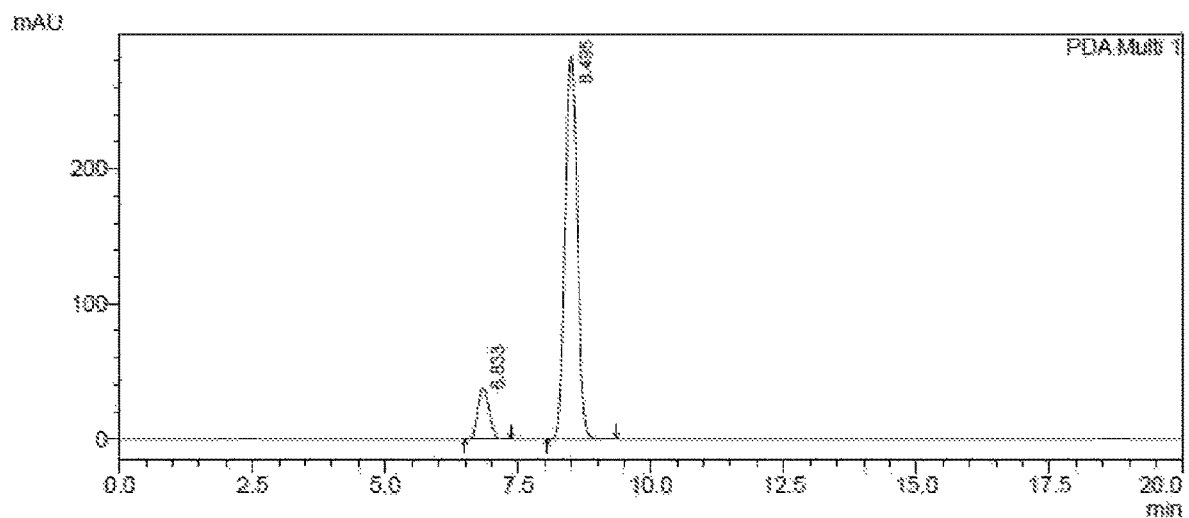

FIG. 7 shows an HPLC chromatogram of the compound 1 prepared according to the method of Comparative Example 1. The ratio of the isomers thereof, i.e., $R_P$-1 to $S_P$-1 is 10.82%: 89.18%, and the peak data thereof is shown as below.

| Peak # | Name | Retention time | Area | Peak height | Area % |
|---|---|---|---|---|---|
| 1 | $R_P$-1 | 6.833 | 554365 | 37166 | 10.82 |
| 2 | $S_P$-1 | 8.495 | 4569402 | 283636 | 89.18 |
| Total | | | 5123768 | 320802 | 100 |

EXAMPLES

The contents of the present disclosure is further explained and described below in conjuction with the Examples. It should be understood that these Examples are merely used to describe the present disclosure but are not intended to limit the scope of the present disclosure. As for the experimental methods whose specific conditions are not indicated in the following Examples, the conditions are usually in accordance with the conventional conditions or the conditions suggested by the manufacturers. Unless otherwise specified, all percentages, rates, ratios, or parts are in terms of weight.

The units in the percent weight in volume in the present disclosure are well known to those skilled in the art and refer to, for example, the weight (g) of a solute per milliliter of a solution. Unless otherwise defined, all the professional and scientific terms used herein have the same meanings as is familiar to one skilled in the art. In addition, any methods and materials similar or equivalent to the described contents can be used in the method of the present disclosure. The preferred embodiments and materials described herein are for illustrative purposes only.

In the present disclosure, the purity of the compound $S_P$-1 is determined by an HPLC method, which is conducted with the following column and conditions: octadecylsilane-bonded silica is used as a filler (YMC-hydrosphere C18 column, 150 mm×4.6 mm, 3 μm), a 0.1% phosphoric acid solution serves as the mobile phase A; methanol-acetonitrile (30:70) serves as the mobile phase B; the gradient elution is run with mobile phase A: mobile phase B=4:1 to 1:4 if necessary; flow rate: 1.0 (mL/min); run time: 46 min; the detection wavelength is 220 nm.

The purity of the compound 61501b of the present disclosure is also determined by an HPLC method, which is conducted with the following column and conditions: YMC hydrosphere 150×4.6 mm, 3 μm; 40% to 85% methanol and 2‰ phosphoric acid/water are used as mobile phases; run time: 46 min; gradient elution and adjusting the proportion of the mobile phase if necessary, flow rate: 1.0 (ml/min).

Example 1 Preparation of the Compound 61502

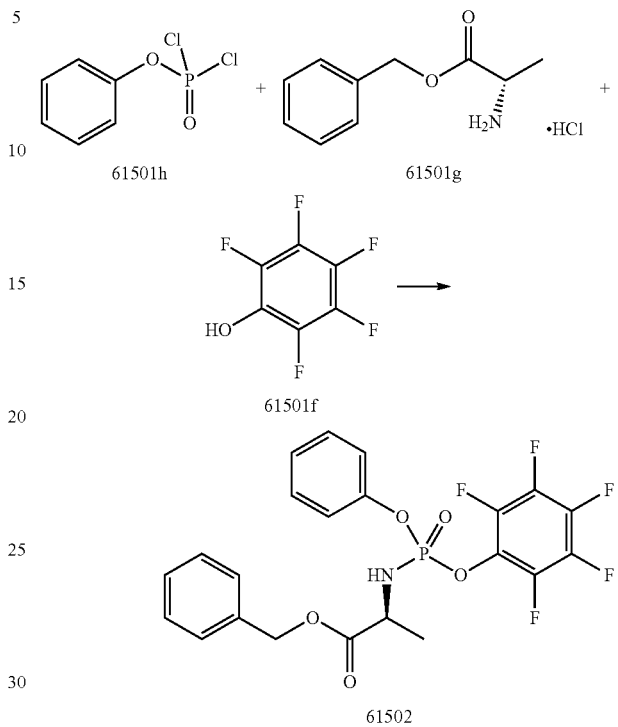

To a solution of 61501h (20 g) in dichloromethane (60 ml) was added 61501g (20.6 g) at −80° C., and then 19.3 g of triethylamine (diluted in 20 ml of dichloromethane) was added. The mixture was stirred overnight at room temperature. To the mixture was added 61501f followed by 19.3 g of triethylamine (diluted in 20 ml of dichloromethane), and the mixture was stirred at room temperature for 4 hours. The mixture was directly deprived of the solvent, and the residue was dissolved in ethyl acetate (200 ml) and water (400 ml); after ethyl acetate was separated, the aqueous phase was washed with ethyl acetate (2×100 ml); the ethyl acetate phases were combined, washed with saline and dried with anhydrous sodium sulfate. Ethyl acetate was eliminated by evaporation to give the target compound (61502), which was used directly in the subsequent purification.

Example 2 Preparation of the Compound 61501b

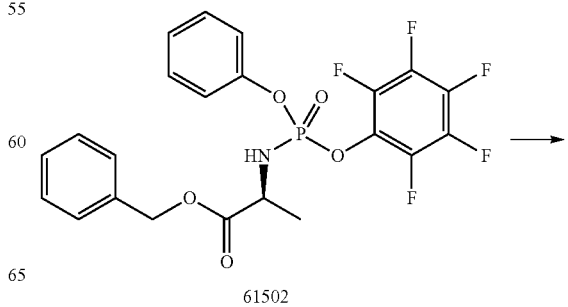

-continued

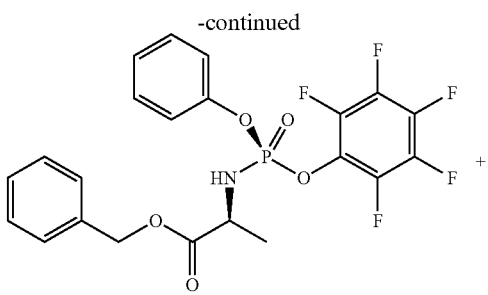

61501e

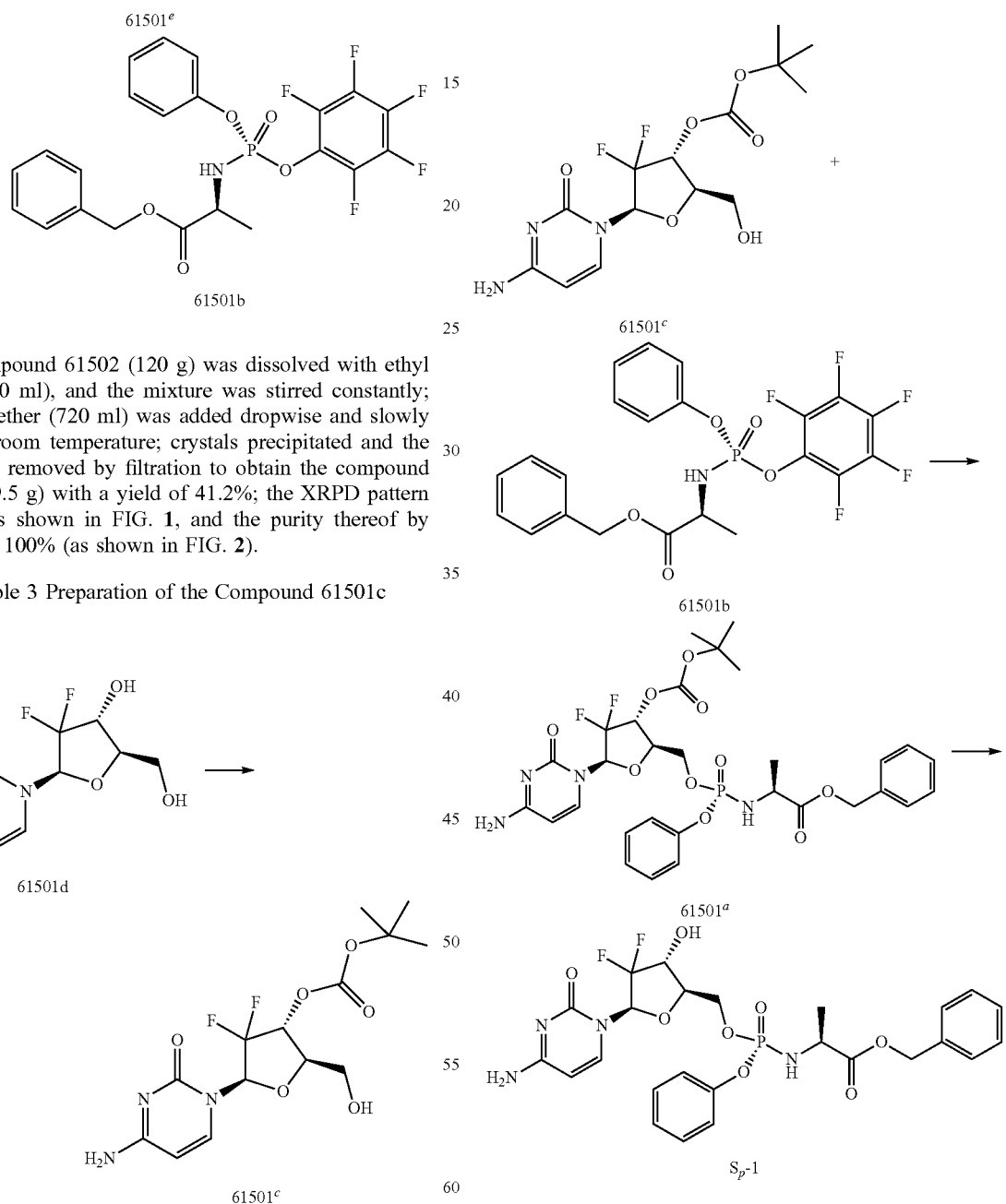

Figure 1:
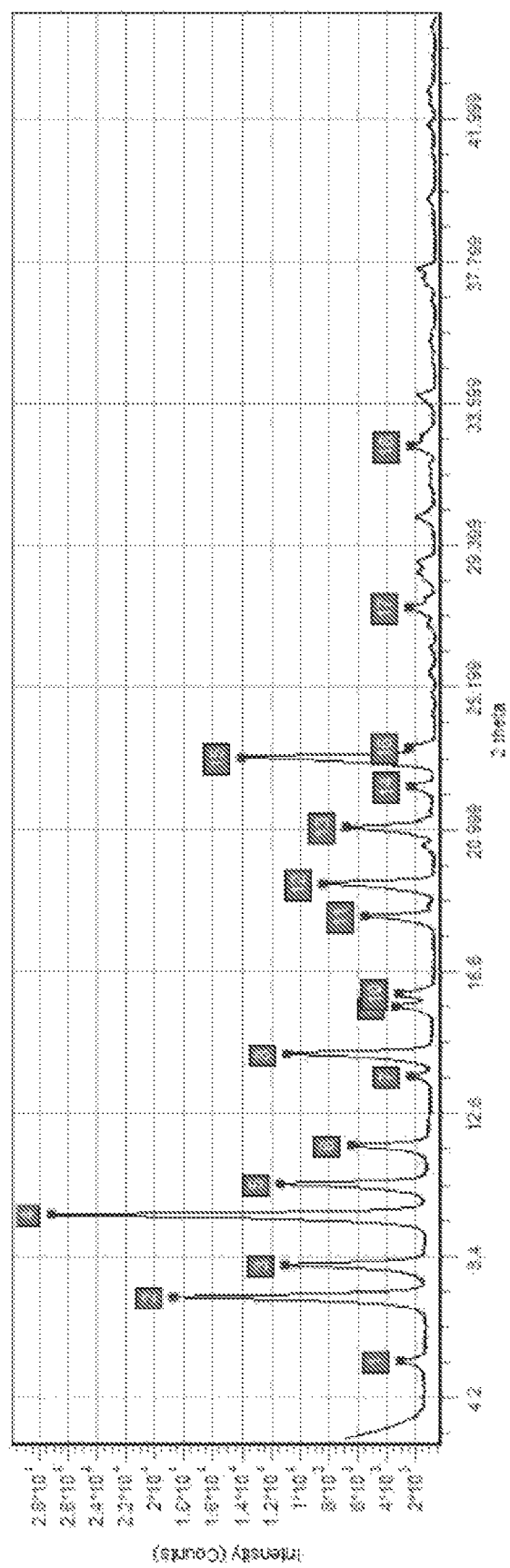

The compound 61502 (120 g) was dissolved with ethyl acetate (240 ml), and the mixture was stirred constantly; petroleum ether (720 ml) was added dropwise and slowly thereto at room temperature; crystals precipitated and the filtrate was removed by filtration to obtain the compound 61501b (49.5 g) with a yield of 41.2%; the XRPD pattern thereof was shown in FIG. 1, and the purity thereof by HPLC was 100% (as shown in FIG. 2).

Example 3 Preparation of the Compound 61501c

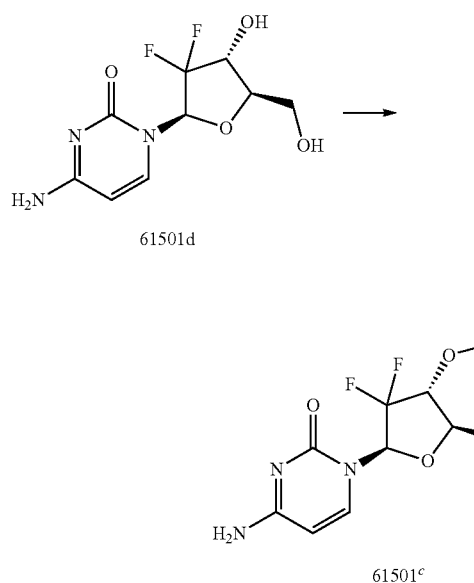

At room temperature, to a mixed solution of the compound 61501d (20 g) in tetrahydrofuran (200 ml) and water (100 ml) was added sodium carbonate (35.4 g), followed by di-tert-butyl dicarbonate (17.5 g), and the mixture was stirred at room temperature until the completion of the reaction. The mixture was subjected to extraction with ethyl acetate (3×200 ml), and ethyl acetate was combined, washed with saline and dried with anhydrous sodium sulfate. After the solvent was eliminated by evaporation, the residue was purified by silica gel chromatography (2.5% to 10% methanol/dichloromethane) to give 18 g of the compound (61501c) with a yield of 67%.

Example 4 Preparation of the Compound $S_P$-1

(1) Preparation of the Compound 61501a: to a solution of the compound 61501c (5 g) in tetrahydrofuran (25 ml) was added a solution of tert-butylmagnesium chloride (1.0 mol/L 41.28 ml) at 0° C.; after stirring and reacting for 1 hour, the compound 61501b (12.42 g) was added and stirred at room temperature till the completion of the reaction. Water (250 ml) was added to the mixture, and the aqueous phase was subjected to extraction with ethyl acetate (3×250 ml); the ethyl acetate phases were combined, washed with saline and dried with anhydrous sodium sulfate; and the solvent was removed. The compound 61501a (6.7 g) was obtained after purification by silica gel column chromatography (mobile phase: methanol/dichloromethane (the proportion of methanol increased from 2.5% to 5%), gradient elution) with a yield of 71.3%.

(2) Preparation of the Compound $S_P$-1: trifluoroacetic acid (20.1 ml) was added to a solution of the compound 61501a (6.7 g) in dichloromethane (33.5 ml) at 0° C., and the mixture was stirred under heat preservation until the reaction was completed. After the mixture was deprived of the solvent, a solution of sodium bicarbonate (150 ml) was added, and the mixture was subjected to extraction with ethyl acetate (3×150 ml); the ethyl acetate phases were combined, washed with saline, and dried with anhydrous sodium sulfate; after the solvent was removed, purification by silica gel column chromatography (mobile phase: methanol/dichloromethane (the proportion of methanol increased from 2.5% to 10%), gradient elution) was performed to give the compound $S_P$-1 (2.7 g, yield: 47%), HPLC purity: 100% (as shown in FIG. 3); $^{31}$P-NMR, (202 MHz, MeOD): $\delta_P$ 3.64. (as shown in FIG. 4); $^1$H-NMR(500 MHz, MeOD): $\delta_H$: 7.56, 7.52 (2d, J=7.5 Hz, 1H, H-6), 7.38-7.33 (m, 7H, ArH), 7.26-7.19 (m, 3H, ArH), 6.25 (apparent q, J=7.5 Hz, 1H, H-1), 5.88, 5.84 (2×d, J=7.5 Hz, 1H, H-5), 5.18-5.12 (m, 2H—OCH$_2$Ph), 4.49-4.42 (m, 1H, H-5'), 4.38-4.31 (m, 1H, H-5'), 4.25-4.18 (m, 1H, H-3'), 4.07-4.01 (m, 2H, H-4', CHCH$_3$), 1.38 (apparent t, J=8.5 Hz, 3H, CHCH$_3$) (as shown in FIG. 5).

Example 5 Preparation of the Compound 61501b

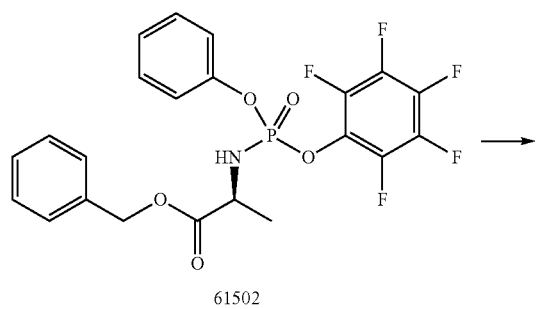

61502

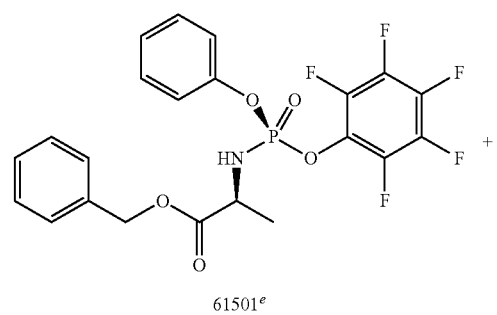

61501$^e$

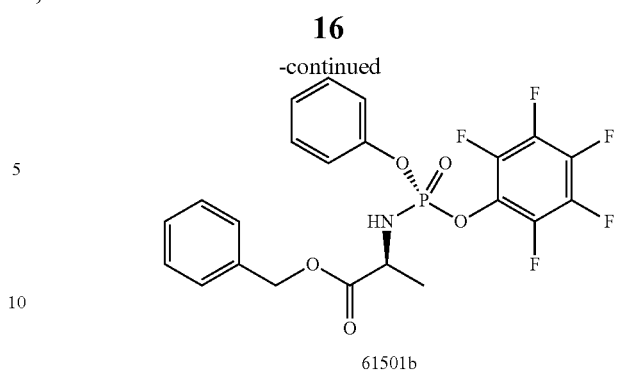

61501b

The compound 61502 (120 g) was dissolved in ethyl acetate (240 ml), and the mixture was stirred constantly at 20° C. to 30° C. for dissolving; petroleum ether (720 ml) was added dropwise and slowly, crystals precipitated and the filtrate was removed by filtration to give the compound 61501b (61.3 g) with a yield of 51%, and the XRPD pattern thereof was shown in FIG. 1, HPLC purity: 99.5%.

Example 6 Preparation of the Compound 61501b

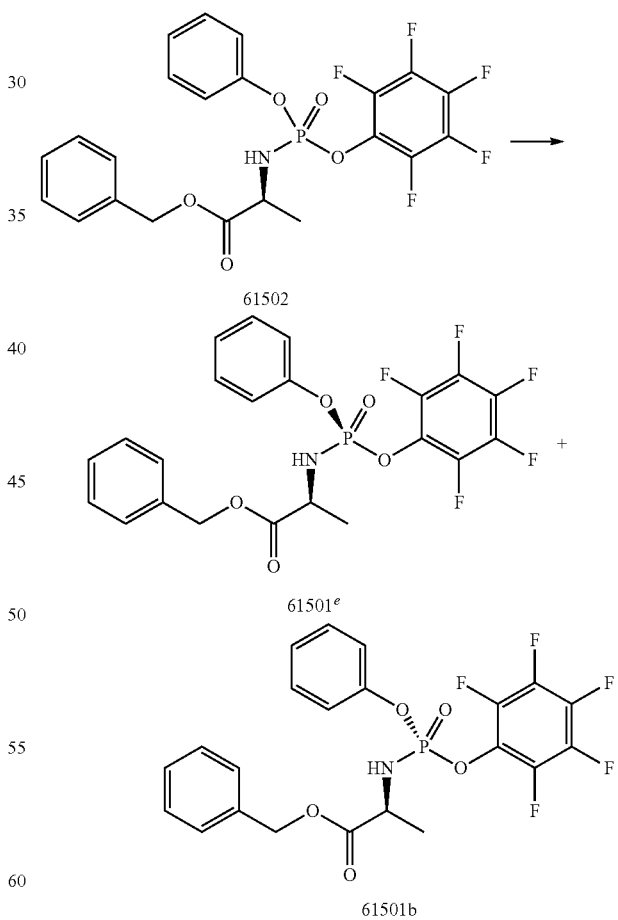

The compound 61502 (120 g) was dissolved in isopropanol (150 ml), and the mixture was stirred constantly at 40° C. to 50° C. for dissolving; petroleum ether (600 ml) was added dropwise and slowly; crystals precipitated and the filtrate was removed by filtration to give the compound 61501b (54.08 g) with a yield of 45%, HPLC purity: 99.1%.

Example 7 Preparation of the Compound 61501b

The compound 61502 (120 g) was dissolved in ethyl acetate (300 ml), and the mixture was stirred constantly at 45° C. to 50° C. for dissolving; petroleum ether (1800 ml) was added dropwise and slowly; crystals precipitated and the filtrate was removed by filtration to give the compound 61501b (57.7 g) with a yield of 48%, and the HPLC purity was shown as 99.8%.

Example 8 Preparation of the Compound 61501b

The compound 61502 (120 g) was dissolved in acetonitrile (1200 ml), and the mixture was stirred constantly at 10° C. to 20° C. for dissolving; hexane (2400 ml) was added dropwise and slowly; crystals precipitated and the filtrate was removed by filtration to give the compound 61501b (36.1 g) with a yield of 30%, HPLC purity: 98.8%.

Comparative Example 1 Preparation of the Compound $S_P$-1 from the Compound 61502

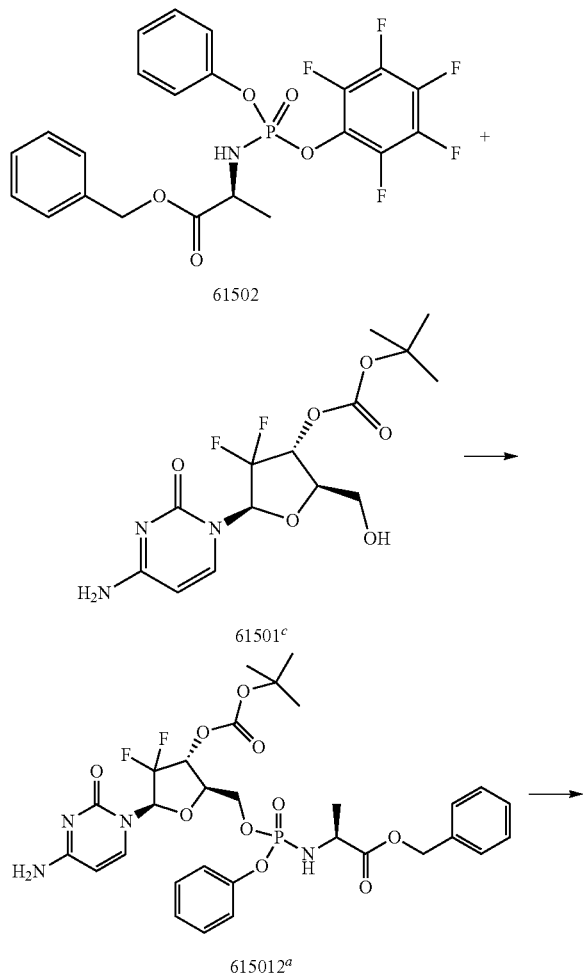

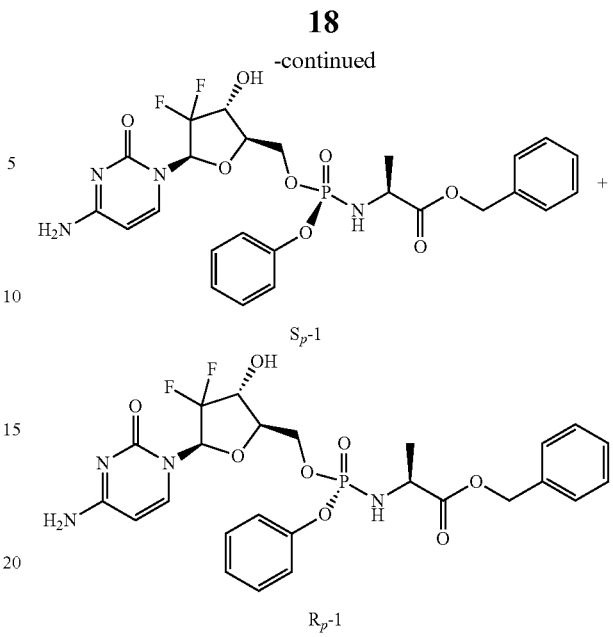

(1) Preparation of the Compound 615012a: to a solution of the compound (61501c) (2 g) in tetrahydrofuran (10 ml) was added a solution of tert-butylmagnesium chloride (1.0 mol/L, 16 ml) at 0° C.; after stirring and reacting for 1 hour, the compound (61502) (5 g) (the ratio of the isomers thereof, i.e., 61501e to 61501b was 26.25%:72.03%, as shown in FIG. 6) was added, and the mixture was stirred at room temperature until the completion of the reaction. Water (50 ml) was added to the mixture and the aqueous phase was subjected to extraction with ethyl acetate (3×100 ml); the ethyl acetate phases were combined, washed with saline and dried with anhydrous sodium sulfate; and the solvent was removed. By purification through silica gel column chromatography (eluent: methanol/dichloromethane: 2.5% to 5%, gradient elution). 1.9 g of the compound (615012a) was obtained with a yield of 53%.

(2) Preparation of the Compound ($S_P$-1): trifluoroacetic acid (12 ml) was added to a solution of the compound (615012a) (3.98 g) in dichloromethane (10 ml) at 0° C., and the mixture was stirred under heat preservation until the reaction was completed. After the mixture was deprived of the solvent, a solution of sodium bicarbonate (100 ml) was added, and the mixture was subjected to extraction with ethyl acetate (3×80 ml); the ethyl acetate phases were combined, washed with saline, and dried with anhydrous sodium sulfate; after the solvent was removed, several purifications by silica gel column chromatography (mobile phase: methanol/dichloromethane (the proportion of methanol increased from 2.5% to 10%), gradient elution) were performed to give the compound (1) (1.1 g); the HPLC detection showed that the ratio of the isomers $R_P$-1 to $S_P$-1 was 10.82%:89.18% (as shown in FIG. 7); $^{31}$P-NMR (202 MHz, MeOD): $\delta_P$ 3.81, 3.64, where $\delta_P$ 3.81 is the absorption site of P in the isomer $R_P$-1, and $\delta_P$ 3.64 is the absorption site of P in the isomer $S_P$-1.

What is claimed is:
1. A method for preparing a composition enriched in a crystalline form of compound 61501b wherein the purity of the compound 61501b is not less than 90%, and
the X-ray powder diffraction pattern of the crystalline form of compound 61501b has peaks at the following 2θ angles: 7.2°±0.3°, 9.6°±0.3° and 23.1°±0.3°, comprising:

reacting a compound (61501h) with a compound (61501g) under alkaline conditions, and then reacting with a compound (61501f) to obtain a compound 61502:

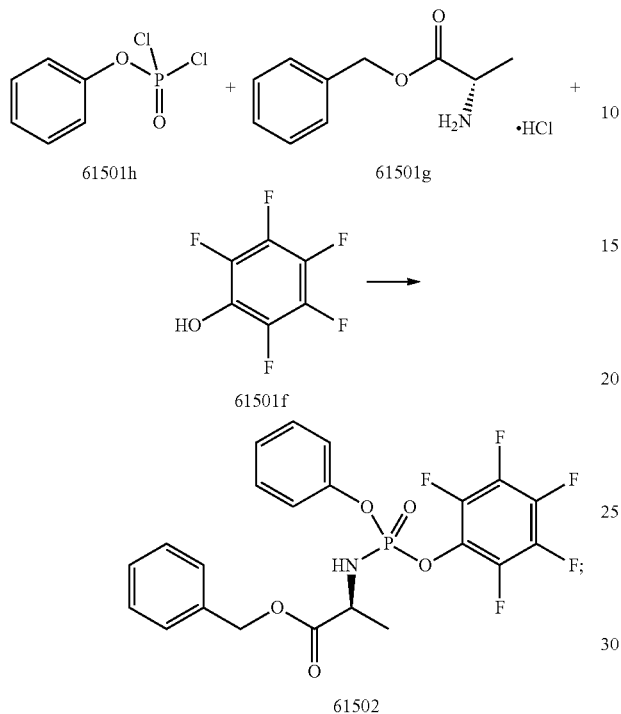

and obtaining the composition enriched in the crystalline form of compound 61501b by isomer separation of the compound 61502, the isomer separation comprising: dissolving the compound 61502 in an organic solvent and stirring for dissolving; and adding an anti-solvent dropwise to the above solution system, and crystallizing, thereby giving the compound 61501b:

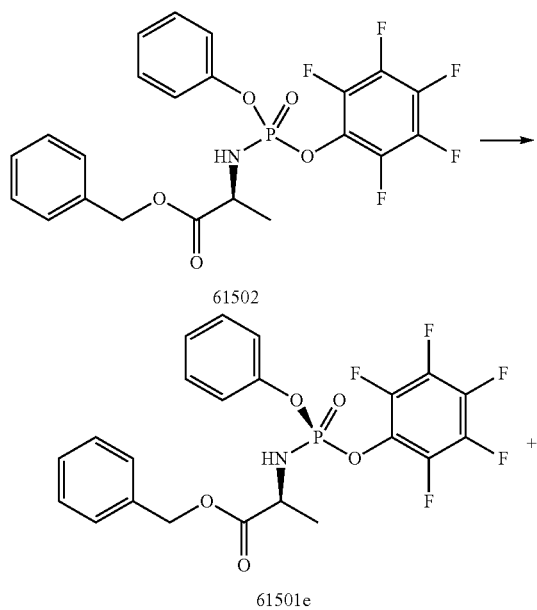

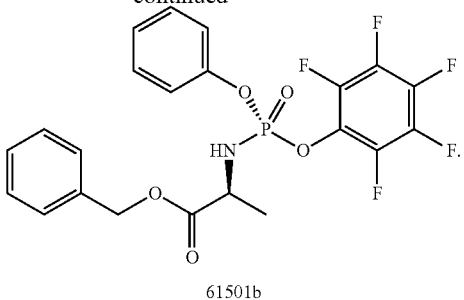

2. The method according to claim 1, wherein the organic solvent comprises at least one of the following: $C_{1-8}$ alcohols, $C_{2-8}$ ethers, $C_{3-7}$ ketones, $C_{3-7}$ esters, $C_{1-2}$ chlorocarbons, and $C_{2-7}$ nitriles.

3. The method according to claim 2, wherein the organic solvent is selected from ethyl acetate, tert-butyl methyl ether, isopropanol or tetrahydrofuran.

4. The method according to claim 1, wherein the anti-solvent comprises at least one of the following: $C_{5-12}$ saturated hydrocarbons, $C_{6-12}$ aromatic hydrocarbons, and petroleum ether.

5. The method according to claim 4, wherein the anti-solvent is selected from petroleum ether or hexane.

6. The method according to claim 1, wherein the volume ratio of the organic solvent to the anti-solvent is 1:4 to 6 (v/v), 1:3 (v/v), or 1:2 (v/v); the amount ratio of the compound 61502 to the organic solvent is 1:1.25 to 2.5 (w/v), or 1:10 (w/v).

7. The method according to claim 1, wherein the organic solvent is selected from ethyl acetate and the anti-solvent is selected from petroleum ether.

8. The method according to claim 1, wherein the isomer separation comprises: dissolving the compound 61502 in ethyl acetate, and stirring at room temperature for dissolving; and adding petroleum ether dropwise to the above solution system, crystallizing and filtering, thereby giving the compound 61501b.

9. The method according to claim 8, wherein the amount ratio of the compound 61502 to ethyl acetate is 1:1.25 to 2.5 (w/v), or 1:10 (w/v), and the amount ratio of ethyl acetate to petroleum ether is 1:4 to 6 (v/v), or 1:3 (v/v).

10. The method according to claim 1, wherein the temperature of the stirring for dissolving and crystallizing is 10° C. to 50° C.

11. The method according to claim 1, wherein the prepared compound 61501b is in crystalline form, and an X-ray powder diffraction pattern of the crystal has peaks at the following 2θ angles: 7.2°±0.3°, 8.1°±0.3°, 9.6°±0.3°, 10.5°±0.3°, 14.4°±0.3° and 23.1°±0.3°.

12. The method according to claim 11, wherein the X-ray powder diffraction pattern of the crystal has peaks at the following 2θ angles: 5.3°±0.3°, 7.2°±0.3°, 8.1°±0.3°, 9.6°±0.3°, 10.5°±0.3°, 11.6°±0.3°, 14.4°±0.3°, 19.4°±0.3°, 21.1°±0.3° and 23.1°±0.3°.

13. The method according to claim 12, wherein the crystal has an X-ray powder diffraction pattern substantially as shown in FIG. 1.

14. A preparation method for a compound Sp-1 comprising:

preparing a composition enriched in a crystalline form of compound 61501b by the method according to claim 4, reacting the composition enriched in a crystalline form of compound 61501b with compound 61501c

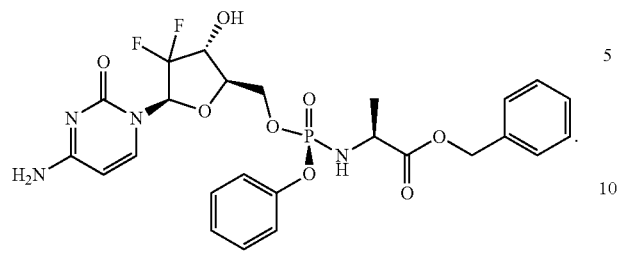
Sp-1
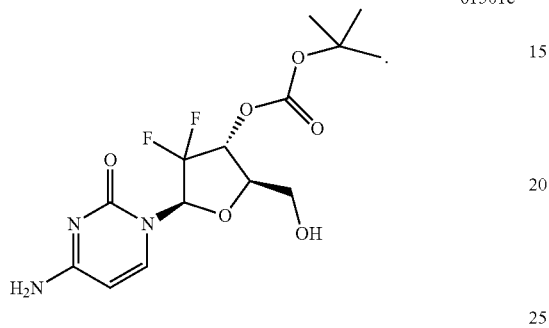
61501c
* * * * *

UNITED STATES PATENT AND TRADEMARK OFFICE
CERTIFICATE OF CORRECTION

PATENT NO. : 10,538,541 B2  
APPLICATION NO. : 15/754318  
DATED : January 21, 2020  
INVENTOR(S) : Jiandong Yuan et al.

Page 1 of 2

It is certified that error appears in the above-identified patent and that said Letters Patent is hereby corrected as shown below:

In the Claims

Column 19, Lines 14-20 (Approx.), Claim 1, delete " 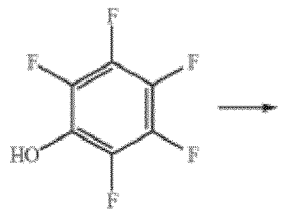 " and insert

-- 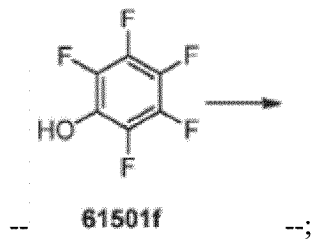 --;

Column 20, Lines 1-13 (Approx.), Claim 1, delete " 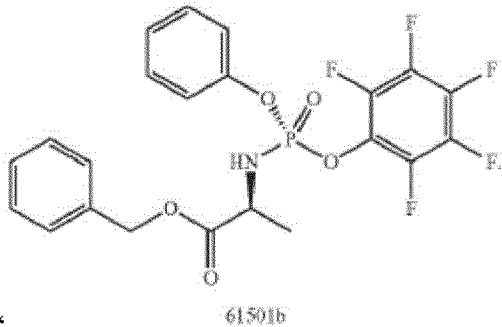 " and

Signed and Sealed this  
Twenty-second Day of December, 2020

Andrei Iancu  
*Director of the United States Patent and Trademark Office*

CERTIFICATE OF CORRECTION (continued)
U.S. Pat. No. 10,538,541 B2

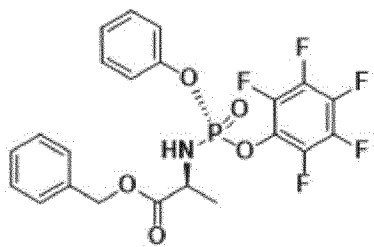

insert --            61501b            --;

Column 20, Line 65, Claim 14, delete "claim 4," and insert -- claim 1, --;

Column 21, Lines 3-25 (Approx.), Claim 14, delete

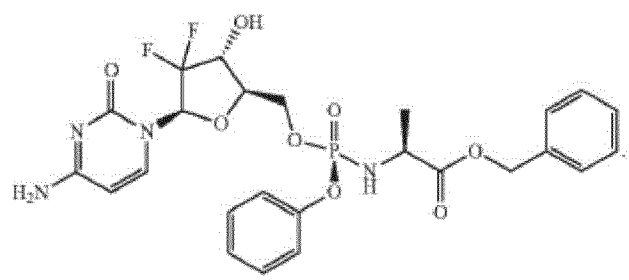

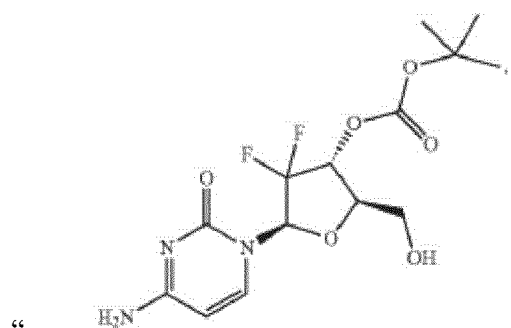

" and insert

-- 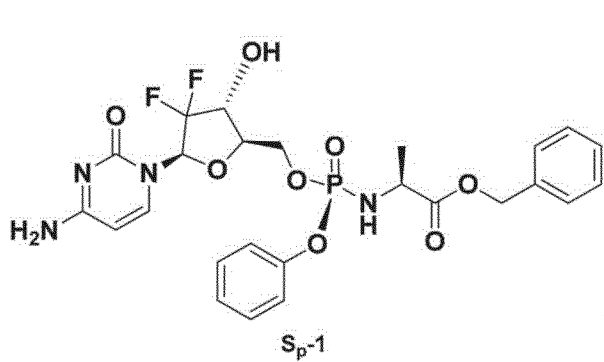 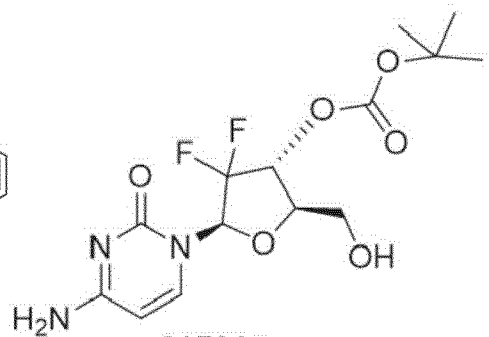 --.